(12) United States Patent
Bedoukian

(10) Patent No.: US 8,551,510 B2
(45) Date of Patent: Oct. 8, 2013

(54) BED BUG CONTROL AND REPELLENCY

(75) Inventor: Robert H. Bedoukian, West Redding, CT (US)

(73) Assignee: Bedoukian Research, Inc., Danbury, CT (US)

( * ) Notice: Subject to any disclaimer, the term of this patent is extended or adjusted under 35 U.S.C. 154(b) by 0 days.

(21) Appl. No.: 13/317,743

(22) Filed: Oct. 27, 2011

(65) Prior Publication Data

US 2012/0046359 A1 Feb. 23, 2012

Related U.S. Application Data

(63) Continuation-in-part of application No. PCT/US2010/001198, filed on Apr. 22, 2010.

(60) Provisional application No. 61/214,766, filed on Apr. 28, 2009.

(51) Int. Cl.
*A01N 25/00* (2006.01)
*A01N 25/34* (2006.01)
*A01N 35/00* (2006.01)

(52) U.S. Cl.
USPC ............ 424/405; 424/403; 514/675; 514/919

(58) Field of Classification Search
None
See application file for complete search history.

(56) References Cited

U.S. PATENT DOCUMENTS

| | | | | |
|---|---|---|---|---|
| 2,283,471 A * | 5/1942 | Swaine | .......................... | 514/688 |
| 3,426,133 A | 2/1969 | Shotton | .......................... | 424/300 |
| 4,548,764 A | 10/1985 | Munteanu | ........................ | 261/75 |
| 5,409,958 A * | 4/1995 | Butler et al. | .................... | 514/690 |
| 6,660,288 B1 * | 12/2003 | Behan et al. | ..................... | 424/405 |
| 7,288,573 B2 | 10/2007 | Roe | ................................ | 514/675 |
| 7,378,557 B1 | 5/2008 | Zhang et al. | .................... | 568/342 |
| 7,381,431 B2 | 6/2008 | Baker et al. | ..................... | 424/725 |
| 2005/0187289 A1 | 8/2005 | Dolan et al. | .................... | 514/457 |
| 2005/0245407 A1 | 11/2005 | Ishihara et al. | ................ | 510/101 |
| 2007/0111918 A1 | 5/2007 | Caswell et al. | ................ | 510/439 |
| 2008/0269177 A1 * | 10/2008 | Bessette | ......................... | 514/163 |
| 2009/0018192 A1 * | 1/2009 | Zhang et al. | ................... | 514/546 |
| 2011/0213038 A1 | 9/2011 | Bedoukian | ..................... | 514/678 |

FOREIGN PATENT DOCUMENTS

WO  WO 0049865 A2 *  8/2000
WO  WO 2007099347 A2 *  9/2007

OTHER PUBLICATIONS

Koul et al (Essential Oils as Green Pesticides: Potential and Constraints, 2008, Biopesticides International, vol. 4, pp. 63-84).*
Ruiz del Castillo et al (Enantiomeric purity of (+/−) methyl jasmonate in fresh leaf samples and commercial fragrances, Jun. 2007, Journal of Separation Science, vol. 30, pp. 2117-2122).*
David J. Moore et al: "Laboratory Evaluation of Insecticide Product for Control of *Cimex lectularius*", Journal of Economic Entomology, vol. 99, No. 6, Dec. 1, 2006.

* cited by examiner

*Primary Examiner* — Brian-Yong Kwon
*Assistant Examiner* — Mark V Stevens
(74) *Attorney, Agent, or Firm* — Ohlandt, Greeley, Ruggiero & Perle, LLP; George W. Rauchfuss, Jr.

(57) ABSTRACT

Control or repellency of bed bugs by bringing the bed bugs into contact with a bed bug control formulation containing at least one compound selected from the group consisting of certain alkyl ketones and cyclic ketones wherein the total number of carbon atoms in the alkyl ketones and cyclic ketones is from 10 to 16 carbon atoms and method for achieving such control or repellency.

22 Claims, No Drawings

BED BUG CONTROL AND REPELLENCY

This application is a continuation-in-part of PCT Application No. PCT/US2010/001198, filed 22 Apr. 2010, and claims priority from US Provisional Application No. 61/214,766 filed Apr. 28, 2009.

FIELD OF THE INVENTION

This invention relates to compositions and methods for the control or repellency of bed bugs

BACKGROUND TO THE INVENTION

There have been a number of publications regarding various characteristics of bed bugs. See generally C. Johnson, The ecology of the bed-bug, *Cimex lectularius* L., 41 Journal of Hygiene 345-461 (1942); H. Levinson et al., Assembling and alerting scents produced by the bedbug, *Cimex lectularius* L., 27 Experientia: 102-103 (1971); H. Levinson et al., Action and composition of the alarm pheromone of the bedbug *Cimex lectularius* L., 61 Naturwissenschaften 684-685 (1974); H. Levinson et al., Structure of sensilla, olfactory perception, and behavior of the bedbug, *Cimex lectularius*, in response to its alarm pheromone, 20 Journal of Insect Physiology 1231-1248 (1974); K. Mellanby, The physiology and activity of the bed-bug (*Cimex lectularius*) in a natural infestation, 31 Parasitology 200-211 (1939); and H. Schmitz et al., The ability of Rhodniusprolixus (Hemiptera; Reduviidae) to approach a thermal source solely by its infrared radiation, 46 Journal of Insect Physiology 745-751 (2000).

Bed bugs feed on human blood. Thus, bed bugs are not merely unsightly, they leave ugly skin markings. However problematic this is for residential bedrooms, it is an even more serious problem for hotels and the like. With respect to such commercial bedrooms there is more opportunity for external infection sources to bring bed bugs to the site, and should there be an unknown infestation which causes biting of customers before it is dealt with, there is a severe risk of customer dissatisfaction and adverse publicity, likely leading to a long term significant reputation loss.

Recent data suggests bed bug infestations (*Cimex* species) of human domiciles are on the rise. At least 92 species of bed bugs have been identified globally, of which at least 16 species are in the North American continent. Generally, bed bugs are parasitic pests with its hosts including humans and various domesticated animals. It is believed that bed bug infestations are becoming more problematic now at least in part because long acting, residual insecticides are no longer being used to keep bedbug populations in check. In addition, increased international travel and insecticide resistance have made bedbug infestations spread and control with insecticides very difficult. In terms of scale, such infestations are of particular concern for hoteliers, cruise ships, trains, daycare facilities, and the like because of the business reputation risk posed by bad press or bad reviews. Other problematic areas tend to include nursing homes, barracks, dorms, hospitals, and various other forms of high density housing. Nonetheless, single-family homes can likewise be impacted adversely.

There have been attempts to control bedbug infestation through applications of insecticidal chemicals to infected areas and materials (especially mattresses). This approach has some drawbacks. For example, it can expose those using a treated area or mattress too soon after application to odor or other undesired characteristics of the pesticidal chemical. Further, unless the chemicals are used regularly, without regard to whether an infestation is is known to already exist (which procedure will significantly increase costs), those sleeping in an infected area can be bitten before one knows to begin treatment.

Bed bugs had nearly been eradicated by the widespread use of potent insecticides such as DDT. However, many of these strong insecticides have been banned from the United States and replaced with weaker insecticides such as pyrethroids. Many bed bugs have grown resistant to the weaker insecticides. In a study at the University of Kentucky bed bugs were randomly collected from across the United States. These "wild" bed bugs were up to several thousands of times more resistant to pyrethroids than were laboratory bed bugs. Another problem with current insecticide use is that the broad-spectrum insecticide sprays for cockroaches and ants that are no longer used had a collateral impact on bedbug infestations. Recently, a switch has been made to bait insecticides that have proven effective against cockroaches but have allowed bed bugs to escape the indirect treatment.

The number of bedbug infestations has risen significantly since the early 21st century. The National Pest Management Association has reported a 71% increase in bedbug calls between 2000 and 2005. The Steritech Group, a pest-management company based in Charlotte, N.C., claimed that 25% of the 700 hotels they surveyed between 2002 and 2006 needed bedbug treatment. In 2003, a brother and sister staying at a Motel 6 in Chicago were awarded $372,000 in punitive damages after being bitten by bedbugs during their stay.

With the widespread use of DDT in the 1940s and 1950s, bed bugs all but disappeared from North America in the mid-twentieth century. Infestations remained common in many other parts of the world and in recent years have also begun to rebound in North America. Reappearance of bed bugs has presented new challenges for pest control without DDT and similarly banned agents.

Another reason for the increase in bed bugs is that pest control services more often nowadays use low toxicity gel-based pesticides for control of cockroaches, the most common pest in structures, instead of residual sprays. When residual sprays meant to kill other insects were commonly being used, they resulted in a collateral insecticidal effect on potential bedbug infestations; the gel-based insecticides primarily used nowadays do not have any effect on bed bugs, as they are incapable of feeding on these baits.

There is, therefore, a need for safe and effective chemicals to control or repel bed bugs and for safe and effective means to employ such chemicals for the control or repellency of bed bugs.

SUMMARY OF THE INVENTION

Safe and effective control or repellency of bed bugs can be accomplished with the use of formulations containing at least one compound selected from alkyl ketones and cyclic ketones wherein the total number of carbon atoms in the alkyl ketones and cyclic ketones is from 10 to 16 carbon atoms and wherein the alkyl or cyclic ketone is selected from the group consisting of geranylacetone (6,10-dimethyl-5,9-undecadien-2-one), methyl undecyl ketone (2-tridecanone), geranylcyclopentanone and also known as apritone (2-(3,7-dimethylocta-2,6-dienyl)cyclopentan-1-one), methyl apritone (2-(3,7-dimethyl-2,6-nonadienyl)cyclopentanone), Velvione™ (5Z) cyclohexadec-5-ene-1-one, methyl dihydrojasmonate (methyl 2-(3-oxo-2-pentylcyclopentyl)acetate), octenylcyclopentanone (2-(2-octen-1-yl)cyclopentanone), methyl decyl ketone (2-dodecanone), nootkatone (4,4a-dimethyl-6-prop-1-en-2-yl-3,4,5,6,7,8-hexahydronaphthalen-2-one), alpha-ionone (4-(2,6,6-trimethyl-2-cyclohexenyl)-3-buten-2-one), beta ionone (4-(2,6,6-trimethyl-1-cyclohexenyl)-3-buten-2-one), alpha-isomethylionone (3-methyl-4-(2,6,6-trimethyl-2-cyclohexen-1-yl)-3-buten-2-one), Nectaryl™ (2-(2-(4-methyl-3-cyclohexen-1-yl) propyl) cyclopentanone), isobutylionone ((E)-5-Methyl-1-(2,6,6-trimethyl-1-cyclohex-2-enyl) hex-1-en-3-one), dimethylionone ((E)-2-methyl-1-(2,2,6-trimethyl-1-cyclohex-3-enyl)pent-1-en-3-one), isolongifolanone (2,2,7,7-tetramethyltricyclo[6.2.1.01,6]undecan-5-one), pseudoionone (6,10-dimethyl-3,5,9-undecatrien-2-one), 2-cyclopentylcyclopentanone, methyl nonyl ketone, 2-decen-2-one, 1-carvone, methyl jasmonate (Z)-methyl 2-(3-oxo-2-(pent-2-enyl)cyclopentyl)acetate, ethyl dihydrojasmonate (ethyl 2-(3-oxo-2-pentylcyclopentyl)acetate), propyl dihydrojasmonate (propyl 2-(3-oxo-2-pentylcyclopentyl)acetate), amyl cyclopentanonepropanone (3-(2-oxopropyl)-2-pentylcyclopentanone), calyxol (ethyl 2-methyl-4-oxo-6-pentylcyclohec-2-enecarboxylate), tetrahydromethylapritone(2-(3,7-dimethynonyl)cyclopentanone), N,N-diethyl-2-(3-oxo-2-oentylcyclopentyl)acetamide and prenyl dihydrojasmonate (3-methylbut-2-enyl 2-(3-oxo-2-pentylcyclopentyl)acetate). Preferred are those alkyl ketones and cyclic ketones that contain from 12 to 16 carbon atoms and especially preferred are those alkyl ketones and cyclic ketones that contain from 13 to 16 carbon atoms. The compounds may be present in any of their isomeric or enantiomeric forms or as mixtures of their isomers or enantiomers. Further aspects of this invention relate to the use of such formulations in various methods for the control or repellency of bed bugs. Among the various methods in which the formulations of this invention may be employed are (1) injecting the formulations into a mattress, either directly or in combination with other ingredients or solvents, (2) placing the formulations on an absorbent material and placing the absorbent material in a sachet and placing the sachet containing the formulation into a locus such as a mattress, hamper, suitcase, clothing bag, linen storage closet or any other enclosure where bed bugs may be present, (3) preparing "dryer sheets" containing the formulations for placement in a locus such as a mattress, suitcase, clothing bag, hamper, clothing bag, linen storage closet, or any other enclosure where bed bugs are likely to be present, or in a pile of clean or soiled or dirty laundry, (4) placing the formulation into detergent or fabric softener compositions for controlling bed bugs during use of these compositions in cleaning clothes and sprays or in carpet or floor cleaner products the like to treat carpets and furniture, and (5) topical application of the formulation intended for use with humans or animals, such as in the form of a lotion, powder, spray or shampoo.

DETAILED DISCLOSURE OF THE INVENTION

Safe and effective control or repellency of bed bugs can be accomplished with the use of formulations containing at least one compound selected from alkyl ketones and cyclic ketones wherein the total number of carbon atoms in the alkyl ketones and cyclic ketones is from 10 to 16 carbon atoms and wherein the alkyl or cyclic ketone is selected from the group consisting of geranylacetone (6,10-dimethyl-5,9-undecadien-2-one), methyl undecyl ketone (2-tridecanone), geranylcyclopentanone and also known as apritone (2-(3,7-dimethylocta-2,6-dienyl)cyclopentan-1-one), methyl apritone (2-(3,7-dimethyl-2,6-nonadienyl)cyclopentanone), Velvione™ (5Z) cyclohexadec-5-ene-1-one, methyl dihydrojasmonate (methyl 2-(3-oxo-2-pentylcyclopentyl)acetate), octenylcyclopentanone (2-(2-octen-1-yl)cyclopentanone), methyl decyl ketone (2-dodecanone), nootkatone (4,4a-dimethyl-6-prop-1-en-2-yl-3,4,5,6,7,8-hexahydronaphthalen-2-one), alpha-ionone (4-(2,6,6-trimethyl-2-cyclohexenyl)-3-buten-2-one), beta ionone (4-(2,6,6-trimethyl-1-cyclohexenyl)-3-buten-2-one), alpha-isomethylionone (3-methyl-4-(2,6,6-trimethyl-2-cyclohexen-1-yl)-3-buten-2-one), Nectaryl™ (2-(2-(4-methyl-3-cyclohexen-1-yl) propyl) cyclopentanone), isobutylionone ((E)-5-Methyl-1-(2,6,6-trimethyl-1-cyclohex-2-enyl) hex-1-en-3-one), dimethylionone ((E)-2-methyl-1-(2,2,6-trimethyl-1-cyclohex-3-enyl)pent-1-en-3-one), isolongifolanone (2,2,7,7-tetramethyltricyclo[6.2.1.01,6]undecan-5-one), pseudoionone (6,10-dimethyl-3,5,9-undecatrien-2-one), 2-cyclopentylcyclopentanone, methyl nonyl ketone, 2-decen-2-one, 1-carvone, methyl jasmonate (Z)-methyl 2-(3-oxo-2-(pent-2-enyl)cyclopentyl)acetate, ethyl dihydrojasmonate (ethyl 2-(3-oxo-2-pentylcyclopentyl)acetate), propyl dihydrojasmonate (propyl 2-(3-oxo-2-pentylcyclopentyl)acetate), amyl cyclopentanonepropanone (3-(2-oxopropyl)-2-pentylcyclopentanone), calyxol (ethyl 2-methyl-4-oxo-6-pentylcyclohec-2-enecarboxylate), tetrahydromethylapritone(2-(3,7-dimethynonyl)cyclopentanone), N,N-diethyl-2-(3-oxo-2-oentylcyclopentyl)acetamide and prenyl dihydrojasmonate (3-methylbut-2-enyl 2-(3-oxo-2-pentylcyclopentyl)acetate). Preferred are those alkyl ketones and cyclic ketones that contain from 12 to 16 carbon atoms and especially preferred are those alkyl ketones and cyclic ketones that contain from 13 to 16 carbon atoms. Preferred examples of the alkyl ketones and cyclic ketones containing from 10 to 16 carbon atoms are geranylacetone (6,10-dimethyl-5,9-undecadien-2-one), methyl undecyl ketone (2-tridecanone), geranylcyclopentanone and also known as apritone (2-(3,7-dimethylocta-2,6-dienyl)cyclopentan-1-one), methyl apritone (2-(3,7-dimethyl-2,6-nonadienyl)cyclopentanone), Velvione™ (5Z) cyclohexadec-5-ene-1-one, methyl dihydrojasmonate (methyl 2-(3-oxo-2-pentylcyclopentyl)acetate), octenylcyclopentanone (2-(2-octen-1-yl)cyclopentanone), methyl decyl ketone (2-dodecanone), nootkatone (4,4a-dimethyl-6-prop-1-en-2-yl-3,4,5,6,7,8-hexahydronaphthalen-2-one), alpha-ionone (4-(2,6,6-trimethyl-2-cyclohexenyl)-3-buten-2-one), beta ionone (4-(2,6,6-trimethyl-1-cyclohexenyl)-3-buten-2-one), alpha-isomethylionone (3-methyl-4-(2,6,6-trimethyl-2-cyclohexen-1-yl)-3-buten-2-one), Nectaryl™ (2-(2-(4-methyl-3-cyclohexen-1-yl) propyl) cyclopentanone), isobutylionone ((E)-5-Methyl-1-(2,6,6-trimethyl-1-cyclohex-2-enyl) hex-1-en-3-one), dimethylionone ((E)-2-methyl-1-(2,2,6-trimethyl-1-cyclohex-3-enyl)pent-1-en-3-one), isolongifolanone (2,2,7,7-tetramethyltricyclo[6.2.1.01,6]undecan-5-one), pseudoionone (6,10-dimethyl-3,5,9-undecatrien-2-one), 2-cyclopentylcyclopentanone, methyl nonyl ketone, 2-decen-2-one, N,N-diethyl-2-(3-oxo-2-oentylcyclopentyl)acetamide and 1-carvone. Especially preferred are octenylcyclopentanone, geranylcyclopentanone, methyl apritone, methyl decyl ketone, Velvione™ and other $C_{15}$-$C_{16}$ cyclic ketones, methyl undecyl ketone and other $C_{13}$-$C_{16}$ methyl ketones, geranylacetone, ionone, nootkatone, and methyl dihydrojasmonate. The most preferred are apritone, methyl apritone, methyl undecyl ketone, and other $C_{15}$-$C_{16}$ cyclic ketones, and methyl dihydrojasmonate, ethyl dihydrojasmonate, propyl dihydrojasmonate and prenyl dihydrojasmonate.

An embodiment of the invention comprises a method for control or repellency of bed bugs by bringing the bed bugs into contact with at least one repellent compound selected from the group consisting of the afore-mentioned alkyl ketones and a cyclic ketones containing from 10 to 16, preferably 12 to 16, and more preferably 13 to 16, carbon atoms such that the bed bugs come into contact with the vapors of the compound(s). The compounds may be present in any of their isomeric or enantiomeric forms or as mixtures of their isomers or enantiomers Another embodiment of this invention comprises a method for control or repellency of bed bugs by placing into an area suspected of possibly containing bed bugs a formulation containing at least one compound selected from the group consisting of an alkyl ketone and a cyclic ketone wherein the total number of carbon atoms in the alkyl ketones and cyclic ketones is from 10 to 16, preferably 12 to 16, and more preferably 13 to 16, carbon atoms such that the bed bugs come into contact with the compound(s) or the vapors of the compound(s). Further embodiments of the invention comprise the aforesaid methods wherein the formulation is sprayed onto or injected into a mattress. Yet another embodiment of the invention comprises the aforesaid methods wherein the formulation is on an absorbent material located in a sachet placed into the suspected area such as a mattress, hamper, suitcase, clothing bag, linen storage closet, or other enclosure where bed bugs may be present. A still further embodiment of the invention comprises the aforesaid methods wherein the formulation is included in a detergent or fabric softener composition. An even still further embodiment of the invention comprises the aforesaid methods wherein the formulation is included in a form similar to a dryer type sheet which may be placed in a mattress, hamper, suitcase, clothing bag, linen storage closet, or in piles of clothes, including clean, dirty or soiled laundry. A still further embodiment of the invention wherein the formulation, preferably in the form of a spray or aerosol, is for application onto or into furniture, fabrics, clothing, footwear, carpets, or luggage (including in public or common areas such as hotels, airplane luggage compartments or other storage facilities to prevent cross contamination). The formulation may be incorporated into a treatment for protecting luggage, furniture, or goods for storage or transport. Dryer sheets are paper or cloth-like sheets generally about one square foot in area that are put into clothes dryers to eliminate static, soften fabrics and add fragrances. A similar dryer sheet type product may be made using the compounds embodied in this invention in place of or in addition to the fragrance. The large surface area of the dryer type sheets will be ideal to promote rapid volatilization of the active ingredients into the areas where bed bugs may be present. Yet another embodiment of this invention comprises the use of said formulations in the aforesaid method wherein the formulation is in a powder form, or as a spray or aerosol, suitable for application to furniture or carpets. Additionally, the aforementioned compound(s) may be incorporated into various home cleaning products for use on carpets, floors, walls, closets, furniture, and the like, or in products intended for human and animal application such as lotions, powders, sprays and shampoos.

The active compound(s) of this invention, the afore-mentioned alkyl ketones and cyclic ketones wherein the total number of carbon atoms in the alkyl ketones and cyclic ketones is from 10 to 16, preferably 12 to 16, and more preferably 13 to 16, carbon atoms, may be employed with any suitable carrier material. The compounds of the formulations of this invention may also be used in conjunction with fragrances, detergents, fabric softeners, as well as with other pesticides with which they may exhibit a synergistic or other beneficial effect.

As used herein, the term "carrier" refers to a material, which may be inorganic or organic and of synthetic or natural origin, with which the active compound is mixed or formulated to facilitate its application to a locus or other object to be treated, or its storage, transport and/or handling. In general, any material that may be customarily employed as a carrier in pesticidal formulations is suitable for use with the present invention. The pesticidal compositions provided herein may be employed alone or in the form of mixtures with such solid and/or liquid dispersible carrier vehicles. As used herein, "carriers" include conventional inert pesticide diluents or extenders of the type usable in conventional pesticide formulations or compositions, e.g., conventional pesticide dispersible carrier vehicles such as solutions, emulsions, suspensions, emulsifiable concentrates, spray powders, pastes, soluble powders, dusting agents, granules, foams, pastes, tablets, aerosols, natural and synthetic materials impregnated with active compounds, microcapsules, fumigating cartridges, fumigating cans and fumigating coils, as well as cold mist and warm mist formulations.

Examples of conventional carrier vehicles for use herein include, but are not limited to, aerosol propellants which are gaseous at normal temperatures and pressures, such as propane, butane, isobutene and carbon dioxide; inert dispersible liquid diluent carriers, including inert organic solvents, such as aromatic hydrocarbons, e.g., benzene, toluene, xylene, alkyl naphthalenes, halogenated aromatic hydrocarbons, cycloalkanes, e.g., cyclohexane, paraffins, e.g., petroleum or mineral oil fractions, chlorinated aliphatic hydrocarbons, e.g., methylene chloride, chloroethylenes, alcohols, e.g., methanol, ethanol, propanol, butanol, ethylene or propylene glycol, as well as ethers and esters thereof, e.g., glycol monomethyl ether, amines, e.g., ethanolamine, amides, e.g., dimethyl formamide, sulfoxides, e.g., dimethyl sulfoxide, acetonitrile, ketones, e.g., acetone, methyl ethyl ketone, methyl isobutyl ketone, cyclohexanone, and/or water, as well as inert dispersible finely divided solid carriers such as ground natural minerals, e.g., kaolins, clays, vermiculite, alumina, silica, chalk, i.e., calcium carbonate, talc, attapulgite, montmorillonite, kieselguhr, and ground synthetic minerals, e.g., highly dispersed silicic acid, and silicates, e.g., alkali silicates The formulations of this invention are formulated to provide a control or repellency effective surface concentration in the locus being treated of from about 1 mcg (microgram) to 5 mg (milligram) per sq inch, or in liquid solutions from 0.01% to 10%, or applied directly at full strength. Topical application may be in the range of from about 0.1% to 100%, more preferably at a concentration from 1% to 15%.

The utility and effectiveness of the invention is illustrated by, but not limited to, the following examples.

This test was undertaken employing unconcealed bugs. Two semicircular discs of filter paper, 9 cm in radius treated with 1 ml of solution to wet the entire surface, one treated with an acetone solution of the test compound and one only acetone treated were placed on the lid of a Petri dish. Five replicates of ten (10) bed bugs were release into the center of the lids of the Petri dish with a choice of the test compound treated or only acetone treated substrate. The distribution of bed bugs was recorded at ½, 2, 1, 2, 6 and 24 hours post-treatment. Paired t-tests were conducted for each treatment to ascertain whether or not there was a statistically significant difference in the number of bed bugs on the treated vs. untreated discs. The results for the test compounds were as set forth in the following Tables 1 and 2 wherein the values represent the percent repellency at the indicated time period.

TABLE 1

| Chemical at 0.5% unless noted otherwise | 0.5 hr | 1 hr | 6 hr | 24 hr | Average |
|---|---|---|---|---|---|
| 2-Octenylcyclopentanone | 100 | 100 | 100 | 100 | 100 |
| 2-Geranylcyclopentanone (Apritone) | 100 | 100 | 100 | 100 | 100 |

TABLE 1-continued

| Chemical at 0.5% unless noted otherwise | 0.5 hr | 1 hr | 6 hr | 24 hr | Average |
|---|---|---|---|---|---|
| Methyl decyl ketone | 100 | 100 | 100 | 100 | 100 |
| Methyl Apritone-at 0.2% | 100 | 100 | 100 | 100 | 100 |
| Cyclohexadec-5-ene-1-one-at 0.1% | 94 | 94 | 100 | 100 | 97 |
| Methyl dihydrojasmonate-at 0.2% | 86 | 96 | 94 | 92 | 92 |
| Methyl jasmonate at 0.2% | 80 | 90 | 90 | 88 | 87 |
| Nootkatone | 100 | 100 | 100 | 100 | 100 |
| Geranylacetone | 100 | 100 | 100 | 100 | 100 |
| Methyl undecyl ketone | 100 | 100 | 100 | 100 | 100 |
| Isobutylionone | 100 | 98 | 94 | 94 | 96.5 |
| Alpha Ionone | 100 | 100 | 100 | 84 | 96 |
| Alpha Isomethylionone | 100 | 100 | 100 | 84 | 96 |
| Nectaryl ™ | 87.8 | 95.9 | 100 | 100 | 95.9 |
| Dimethylionone | 90 | 96 | 96 | 92 | 93.5 |
| Isolongifolanone | 90 | 88 | 98 | 98 | 93 |
| 1-Carvone (1% Spearmint Oil containing 80% 1-Carvone) | 82 | 84 | 94 | 80 | 85 |
| 2-Cyclopentylcyclopentanone | 90 | 90 | 76 | 70 | 81 |
| Methyl nonyl ketone | 85.7 | 84 | 80 | 74 | 80.9 |
| 3-Decen-2-one | 82 | 84 | 78 | 76 | 80 |
| 2,3-Undecanedione | 90 | 60 | 60 | 90 | 75 |
| Butyl levulinate at 0.2% | 64 | 68 | 62 | 60 | 64 |

TABLE 2

| Chemical at % indicated | 2 hour |
|---|---|
| Nootkatone at 0.1% | 60 |
| Tetrahydroapritoneat 0.2% | 82 |
| Methyl apritone at 0.2% | 90 |
| Tetrahydro methyl apritone at 0.2% | 88 |
| Methyl dihydrojasmonate at 0.2% | 98 |
| Ethyl dihydrojasmonate at 0.2% | 90 |
| Propyl dihydrojasmonate at 0.2% | 78 |
| Prenyl dihydrojasmonate at 1.0% | 82 |
| Ethyl 2-methyl-4-oxo-6-pentylcyclohex-2-ene-1-carboxylate at 0.2% | 62 |

While the exact mechanism of the superiority of the compounds of this invention containing from 12 to 16 carbon atoms relative to compounds of this invention having less than 12 carbon atoms or more than 16 carbon atoms is not known for sure it is thought to relate to the fit of the compounds with receptors or binding proteins of the bedbugs.

While the invention has been described herein with reference to the specific embodiments thereof, it will be appreciated that changes, modification and variations can be made without departing from the scope of the inventive concept disclosed herein. Accordingly, it is intended to embrace all such changes, modification and variations that fall with the scope of the appended claims.

The invention claimed is:

1. A method for control or repellency of *Cimex* species comprising bringing the *Cimex* species into direct contact or contact with vapors of at least one compound in a *Cimex* species control formulation containing the at least one compound that is an alkyl ketone or cyclic ketone having a total number of carbon atoms in the alkyl ketone or cyclic ketone of from 10 to 16 carbon atoms; and wherein the at least one compound that is an alkyl or cyclic ketone from 10 to 16 carbon atoms is selected from the group consisting of geranylcyclopentanone (apritone), methyl apritone (2-(3,7-dimethyl-2,6-nonadienyl)-cyclopentanone), (5Z) cyclohexadec-5-ene-1-one, methyl dihydrojasmonate (methyl 2-(3-oxo-2-pentylcyclopentyl)acetate), octenylcyclopentanone (2-(2-octen-1-yl)-cyclopentanone), nootkatone (4,4a-dimethyl-6-prop-1-en-2-yl-3,4,5,6,7,8-hexahydronaphthalen-2-one), alpha-isomethylionone (3-methyl-4-(2,6,6-trimethyl-2-cyclohexen-1-yl)-3-buten-2-one), (2-(2-(4-methyl-3-cyclohexen-1-yl) propyl)cyclopentanone), isobutylionone ((E)-5-Methyl-1-(2,6,6-trimethyl-1-cyclohex-2-enyl) hex-1-en-3-one), dimethylionone ((E)-2-methyl-1-(2,2,6-trimethyl-1-cyclohex-3-enyl) pent-1-en-3-one), 2-cyclopentylcyclopentanone, methyl jasmonate ((Z)-methyl 2-(3-oxo-2-(pent-2-enyl)cyclopentyl)acetate), ethyl dihydrojasmonate (ethyl 2-(3-oxo-2-pentylcyclopentyl)acetate), propyl dihydrojasmonate (propyl 2-(3-oxo-2-pentylcyclopentyl) acetate), amyl cyclopentanone propanone (3-(2-oxopropyl)-2-pentylcyclopentanone), calyxol (ethyl 2-methyl-4-oxo-6-pentylcyclohec-2-enecarboxylate), tetrahydromethylapritone (2-(3,7-dimethynonyl)cyclopentanone), N,N-diethyl-2-(3-oxo-2-pentylcyclopentyl)acetamide and prenyl dihydrojasmonate (3-methylbut-2-enyl 2-(3-oxo-2-pentylcyclopentyl)acetate); wherein the *Cimex* control formulations are formulated with the at least one compound that is an alkyl or cyclic ketone from 10 to 16 carbon atoms to provide a control or repellency when effective surface concentrations of the at least one compound in a locus to be treated for *Cimex* of from 1 mcg (microgram) to 5 mg (milligram) per square inch, in liquid solutions from 0.01% to 10%, applied directly to the locus at full strength, or in topical application in the range of from about 0.1% to 100%.

2. The A method according to claim 1, wherein the formulation contains the at least one compound selected from the group consisting of geranylcyclopentanone (apritone), methyl apritone (2-(3,7-dimethyl-2,6-nonadienyl)-cyclopentanone), (5Z)cyclohexadec-5-ene-1-one, methyl dihydrojasmonate (methyl 2-(3-oxo-2-pentylcyclopentyl)acetate), octenylcyclopentanone (2-(2-octen-1-yl)-cyclopentanone), nootkatone (4,4a-dimethyl-6-prop-1-en-2-yl-3,4,5,6,7,8-hexahydronaphthalen-2-one), alpha-isomethylionone (3-methyl-4-(2,6,6-trimethyl-2-cyclohexen-1-yl)-3-buten-2-one), (2-(2-(4-methyl-3-cyclohexen-1-yl)propyl)cyclopentanone), isobutylionone ((E)-5-Methyl-1-(2,6,6-trimethyl-1-cyclohex-2-enyl)hex-1-en-3-one), dimethylionone ((E)-2-methyl-1-(2,2,6-trimethyl-1-cyclohex-3-enyl)pent-1-en-3-one), and 2-cyclopentylcyclopentanone.

3. The method according to claim 1 wherein the formulation contains a cyclic ketone wherein the total number of carbon atoms in the cyclic ketones is from 10 to 16 carbon atoms.

4. The method according to claim 1, wherein the formulation contains the compound selected from the group consisting of geranylcyclopentanone and octenylcyclopentanone.

5. The method according to claim 1, wherein the formulation contains the compound selected from the group consisting of methyl jasmonate, methyl dihydrojasmonate, ethyl dihydrojasmonate, propyl dihydrojasmonate and prenyl dihydrojasmonate.

6. The method according to claim 1 wherein the formulation contains nootkatone.

7. The method according to claim 1 wherein the formulation contains (2-(2-(4-methyl-3-cyclohexen-1-yl) propyl)cyclopentanone).

8. The method according to claim 1 wherein the formulation is sprayed onto or injected into a mattress.

9. A method according to claim 1 wherein the formulation is on an absorbent material located in a sachet placed into the suspected area.

10. The method according to claim 9 wherein the sachet is placed in a locus selected from a mattress, hamper, suitcase, clothing bag, or linen storage closet.

11. The method according to claim 1 wherein the formulation is included in a detergent or fabric softener composition.

12. The method according to claim 1 wherein the formulation is included in a dryer type sheet.

13. The method according to claim 12 wherein the dryer type sheet is placed in a locus selected from a mattress, hamper, suitcase, clothing bag, and linen storage closet.

14. The method according to claim 12 wherein the dryer type sheet is placed in a pile of clean, soiled or dirty laundry.

15. The method according to claim 1 wherein the formulation is placed on or in a carpet or furniture.

16. The method according to claim 1 wherein the formulation is sprayed onto or placed in a fabric, furniture, clothing, footwear, carpet or luggage.

17. The method according to claim 1 wherein the formulation is incorporated into a detergent, fabric softener, carpet or floor cleaner.

18. The method according to claim 1 wherein the formulation is incorporated into a treatment for protecting luggage, furniture, or goods for storage or transport.

19. The method according to claim 1 wherein the at least one compound is incorporated into a formulation for topical application to a human or animal.

20. The method according to claim 19 wherein the at least one compound is incorporated into a shampoo formulation.

21. The method according to claim 1, wherein the total number of carbon atoms in the alkyl ketones and cyclic ketones is from 12 to 16 carbon atoms.

22. A method for control or repellency of *Cimex* species comprising placing into an area suspected of possibly containing *Cimex* species a formulation containing at least one compound that is a selected from the group consisting of an alkyl ketone or cyclic ketone having a total number of carbon atoms in the alkyl ketone or cyclic ketone of from 10 to 16 carbon atoms and wherein the at least one compound that is an alkyl or cyclic ketone from 10 to 16 carbon atoms is selected from the group consisting of geranylcyclopentanone (apritone), methyl apritone (2-(3,7-dimethyl-2,6-nonadienyl)-cyclopentanone), (5Z) cyclohexadec-5-ene-1-one, methyl dihydrojasmonate (methyl 2-(3-oxo-2-pentylcyclopentyl) acetate), octenylcyclopentanone (2-(2-octen-1-yl)-cyclopentanone), nootkatone (4,4a-dimethyl-6-prop-1-en-2-yl-3,4,5,6,7,8-hexahydronaphthalen-2-one), alpha-isomethylionone (3-methyl-4-(2,6,6-trimethyl-2-cyclohexen-1-yl)-3-buten-2-one), (2-(2-(4-methyl-3-cyclohexen-1-yl)propyl)cyclopentanone), isobutylionone ((E)-5-Methyl-1-(2,6,6-trimethyl-1-cyclohex-2-enyl)hex-1-en-3-one), dimethylionone ((E)-2-methyl-1-(2,2,6-trimethyl-1-cyclohex-3-enyl)pent-1-en-3-one), 2-cyclopentylcyclopentanone, methyl jasmonate ((Z)-methyl 2-(3-oxo-2-(pent-2-enyl)cyclopentyl)acetate), ethyl dihydrojasmonate (ethyl 2-(3-oxo-2-pentylcyclopentyl)acetate), propyl dihydrojasmonate (propyl 2-(3-oxo-2-pentylcyclopentyl)acetate), amyl cyclopentanone propanone (3-(2-oxopropyl)-2-pentylcyclopentanone), calyxol (ethyl 2-methyl-4-oxo-6-pentylcyclohec-2-enecarboxylate), tetrahydromethylapritone (2-(3,7-dimethynonyl)cyclopentanone), N,N-diethyl-2-(3-oxo-2-pentylcyclopentyl)acetamide and prenyl dihydrojasmonate (3-methylbut-2-enyl 2-(3-oxo-2-pentylcyclopentyl)acetate);

wherein the *Cimex* control formulations are formulated with the at least one compound that is an alkyl or cyclic ketone from 10 to 16 carbon atoms to provide a control or repellency when effective surface concentrations of the at least one compound in a locus to be treated for suspected *Cimex* of from 1 mcg (microgram) to 5 mg (milligram) per square inch, in liquid solutions from 0.01% to 10%, applied directly to the locus at full strength, or in topical application in the range of from about 0.1% to 100%;

such that the *Cimex* are contacted with the vapor from the at least one compound in the formulation so that direct contact with the liquid or formulated application method is not necessary.

* * * * *